US011754475B2

(12) United States Patent
Park et al.

(10) Patent No.: US 11,754,475 B2
(45) Date of Patent: Sep. 12, 2023

(54) PERSONAL SAMPLER FOR BIOAEROSOL

(71) Applicants: Purdue Research Foundation, West Lafayette, IN (US); Yeungnam University, Gyeongsan (KR)

(72) Inventors: Jae Hong Park, West Lafayette, IN (US); Jeong Hoon Byeon, Gyeongsan (KR)

(73) Assignees: Purdue Research Foundation, West Lafayette, IN (US); Yeungnam University, Gyeongsan (KR)

(*) Notice: Subject to any disclaimer, the term of this patent is extended or adjusted under 35 U.S.C. 154(b) by 809 days.

(21) Appl. No.: 16/558,361

(22) Filed: Sep. 3, 2019

(65) Prior Publication Data

US 2020/0110008 A1 Apr. 9, 2020

Related U.S. Application Data

(60) Provisional application No. 62/741,004, filed on Oct. 4, 2018.

(51) Int. Cl.
 *G01N 1/22* (2006.01)
 *G01N 1/24* (2006.01)
 *G01N 21/76* (2006.01)
 *G01N 33/58* (2006.01)
 *G01N 1/02* (2006.01)
 *C12Q 1/56* (2006.01)

(52) U.S. Cl.
 CPC ............. *G01N 1/2273* (2013.01); *G01N 1/24* (2013.01); *G01N 21/763* (2013.01); *G01N 33/582* (2013.01); *G01N 2001/028* (2013.01); *G01N 2001/2276* (2013.01)

(58) Field of Classification Search
 CPC ...... G01N 1/2273; G01N 1/24; G01N 21/763; G01N 33/582; G01N 2001/028; G01N 2001/2276; G01N 1/2208; C12Q 1/56
 See application file for complete search history.

(56) References Cited

U.S. PATENT DOCUMENTS

| 5,902,385 | A | 5/1999 | Willeke et al. | |
|---|---|---|---|---|
| 6,544,729 | B2 | 4/2003 | Sayler et al. | |
| 7,563,615 | B2 | 7/2009 | Ponce | |
| 2004/0245125 | A1* | 12/2004 | Trkulja | A61B 10/0045 206/223 |
| 2013/0220034 | A1* | 8/2013 | Peters | G01N 1/2273 73/863.22 |

FOREIGN PATENT DOCUMENTS

KR 101754794 B1 * 7/2017 ........... G01N 1/2208

OTHER PUBLICATIONS

Wang et a., "In Situ Rapid Evaluation of Indoor Bioaerosols Using an ATP Bioluminescence Assay"; 2013 (Year: 2013).*
"SKC Respirable Dust Cyclone Performance Guide"; SKC, Inc.*

(Continued)

*Primary Examiner* — Herbert K Roberts
*Assistant Examiner* — Anthony W Megna Fuentes
(74) *Attorney, Agent, or Firm* — Brown Rudnick LLP; Adam M. Schoen

(57) ABSTRACT

The present disclosure relates to a novel personal sampler for bioaerosols and the method of making and using the personal sampler.

7 Claims, 8 Drawing Sheets

(56) References Cited

OTHER PUBLICATIONS

Khan et al., "Indigenous development of an aerodynamic size separator for aerosol size distribution studies"; May 2005 (Year: 2005).*

Park, Ji-Woon, Fast Monitoring of Indoor Bioaerosol Concentrations with ATP Bioluminescence Assay Using an Electrostatic Rod-Type Sampler. PLoS One. 2015; 10(5): e0125251, https://doi.org/10.1371/journal.pone.0125251.

Fabian, P., Airborne influenza virus detection with four aerosol samplers using molecular and infectivity assays: considerations for a new infectious virus aerosol sampler. Indoor Air. Oct. 2009; 19(5): 433-441.

* cited by examiner

FIG. 1

PERSONAL SAMPLER FOR BIOAEROSOL

CROSS-REFERENCE TO RELATED APPLICATION

This application claims the benefits of U.S. Provisional Application Ser. No. 62/741,004, filed Oct. 4, 2018, the contents of which are incorporated herein entirely.

TECHNICAL FIELD

The present disclosure relates to a novel personal sampler for bioaerosols and the method of making and using the personal sampler.

BACKGROUND

This section introduces aspects that may help facilitate a better understanding of the disclosure. Accordingly, these statements are to be read in this light and are not to be understood as admissions about what is or is not prior art.

Bioaerosols are aerosol particles of biological origins that consist of virus, live or dead organisms (e.g., bacteria and fungi cell), and fragments organisms (e.g., bacterial endotoxins, mycotoxins, fungal spores, pollen, animal debris, fragments of biofilm). They are ubiquitous in all occupational and environmental atmospheres. Exposure to bioaerosols greatly increase the risk for acute and chronic diseases, including contagious infectious disease, acute toxic effects, allergies, and cancer. Workers in waste sorting and composting industries frequently suffer from respiratory and airway inflammations, which are linked to the exposure of high-level microorganisms. At agricultural work places, high concentrations ($10^5 \sim 10^7$ CFU/m$^3$) of bacteria and fungi cause infections, allergies, and even death to those in frequent or chronic contact. The monitoring of bioaerosols is essential for controlling air quality, assessing the exposure, identifying sources of bioaerosols, and eventually protecting people's health.

Currently, assessment of the concentrations and content of bioaerosols involves collection into culture media by samplers (e.g., impactors and impingers) and quantification via colony counting. However, this method is time-consuming, and difficult to apply in-sit, due to collection, transport to a lab for 24 hour incubation, and subsequent analysis. Other limitations include: 1) Maximum CFU value is limited by number of impactor nozzles (e.g., 400 holes per stage for Anderson cascade impactor); 2) Knowledgeable selection of agar is required; 3) condensation from agar can cause cross contamination. Moreover, viable bacteria sampling is limited to short sampling times (to reduce loss of viability) and may introduce significant measurement error.

Taking into account the defects of colony counting after sampling, development of a bioaerosol sampler which could be rapid, reliable, and portable would be extremely useful.

SUMMARY

The present disclosure to a novel personal sampler for bioaerosols and the method of making and using the personal sampler.

In one embodiment, the present disclosure provides a novel sampler for bioaerosols, wherein the sampler comprises: a) a bioaerosol receiving element with a tip capable of capturing bioaerosol onto the tip of the bioaerosol receiving element;

b) an impactor element with suitable size to allow a bioaerosol sample to pass, wherein the impactor element comprises an impactor nozzle plate and an impactor housing; and c) a bioaerosol receiving element holder comprising a chamber that hosts the bioaerosol receiving element;

wherein the impactor element separates the bioaerosol receiving element and outside environment from where a bioaerosol sample is collected.

BRIEF DESCRIPTION OF THE DRAWINGS

FIG. 1 shows the basic concept of an adenosine triphosphate (ATP) bioaerosol sampler.

DETAILED DESCRIPTION

Figure 2:
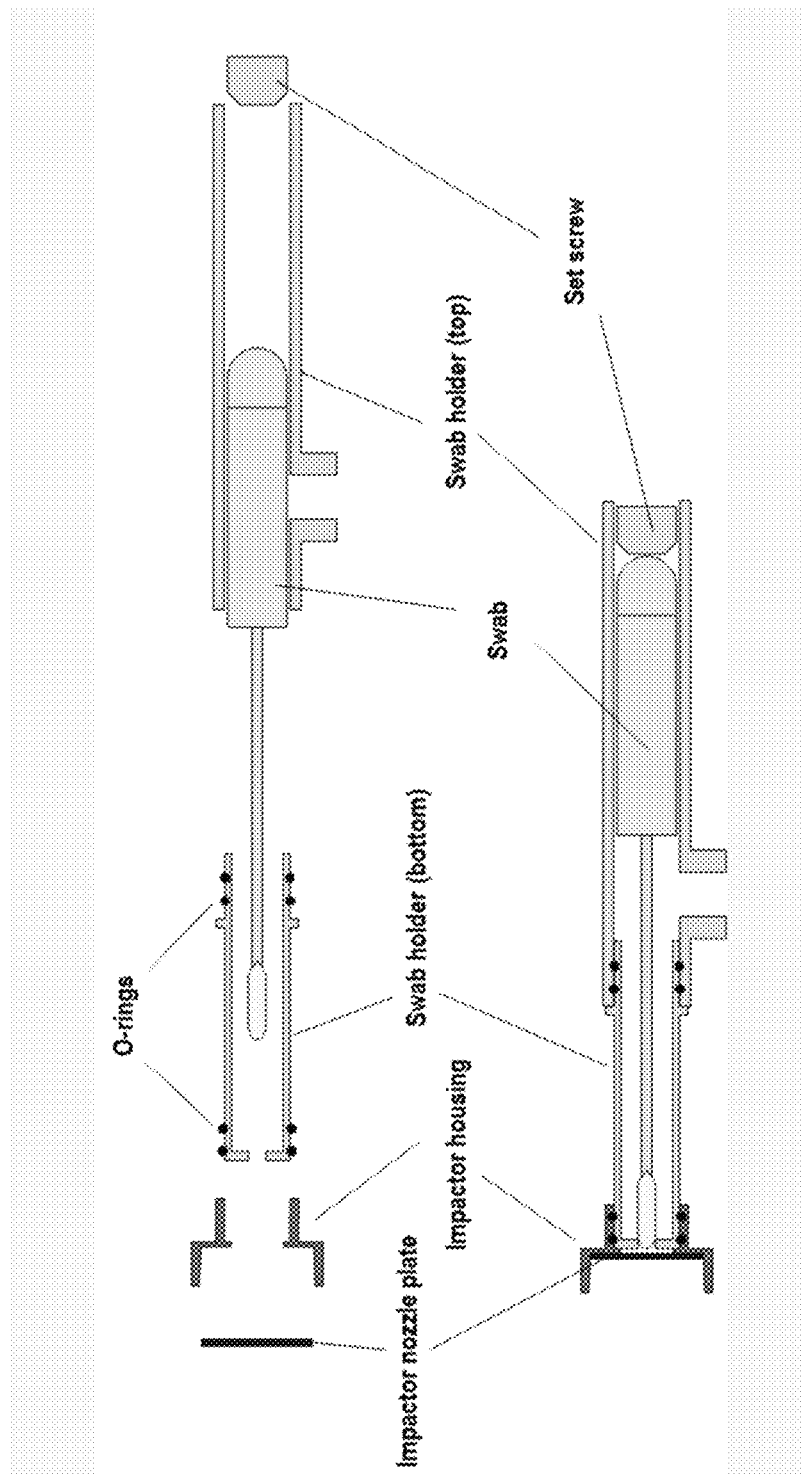
FIG. 2 shows the design of a novel personal sampler for bioaerosol.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "bioaerosol" refers to tiny airborne particles that are biological in nature. That means they either come from a living organism (such as dander from indoor pets or pollen from trees) or are living organisms themselves (such as bacteria and viruses). For example, "bioaerosol" may include but is not limited to dust containing (combined with) microbes.

ATP bioluminescence method quantifies bacteria by measuring the light produced through ATP's reaction with enzyme luciferase. The ATP bioluminescence method was originally designed to measure the bacterial concentration on the surface without incubation. It takes less than 20 seconds for one measurement. The efficiency of the ATP bioluminescence assay has been evaluated in many research and most of these studies are done by comparison experiments with colony counting method. To date, this method has been utilized for surface hygiene analysis other than bioaerosol.

Figure 1:
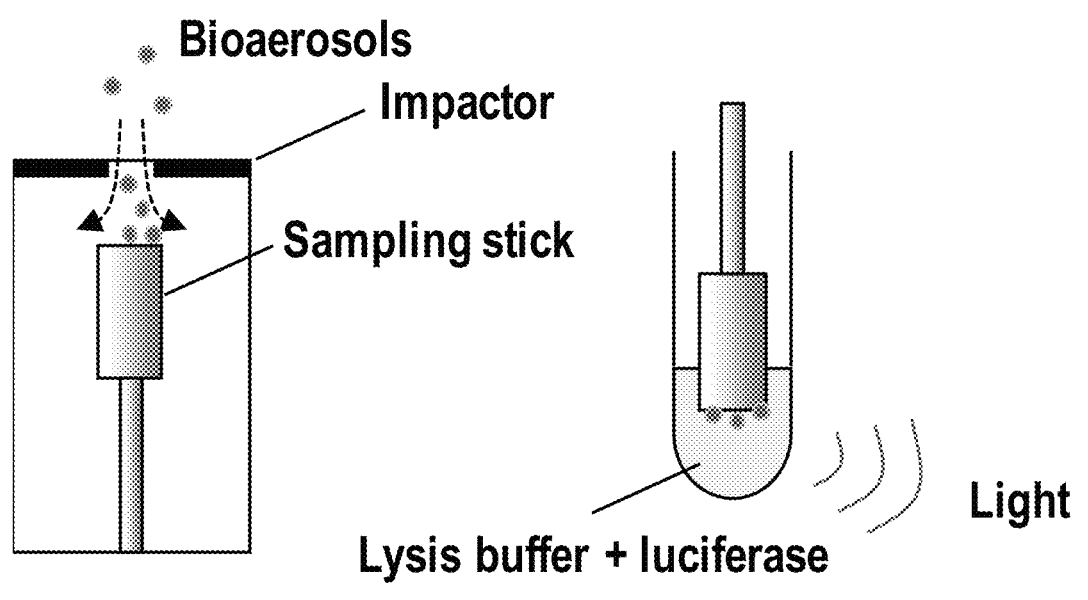

The present disclosure provides a sampler to collect bioaerosols directly onto a swab head used for bioluminescence monitor. See FIG. 1 to FIG. 3. Furthermore, a respirable cyclone was provided to remove particles bigger than 10 μm ($d_{50}$=4 μm) and modified an impactor to have the cut-off diameter of 600 nm. The sampler is operated at the flowrate of 2.5 L/min and available to use with conventional sampling pumps. After sampling the airborne bacteria, swab will be located from the sampler to a bioluminescence monitor to measure the bacteria concentration in relative light units (RLUs).

In one embodiment, the present disclosure provides a sampler for collecting bioaerosols, wherein the sampler comprises:
a) a bioaerosol receiving element with a tip capable of capturing bioaerosol onto the tip of the bioaerosol receiving element;
b) an impactor element with suitable size to allow a bioaerosol sample to pass, wherein the impactor element comprises an impactor nozzle plate and an impactor housing; and
c) a bioaerosol receiving element holder comprising a chamber that hosts the bioaerosol receiving element;
wherein the impactor element separates the bioaerosol receiving element and outside environment from where a bioaerosol sample is collected.

In one embodiment regarding sampler for collecting bioaerosols, the bioaerosol receiving element holder further comprises a detachable first section and a second section, wherein the first section is configured to hold opposite side of the tip of the bioaerosol receiving element and is configured to load and unload the bioaerosol receiving element, wherein the second section has a first end with a hole to allow the tip to contact the impactor element and a second end to attach to the detachable first section of the bioaerosol receiving element holder.

In one embodiment regarding sampler for collecting bioaerosols, the bioaerosol receiving element is a swab configured to collect the bioaerosol sample. Actually, any porous media such as a foam, sponge, puff, or sintered metal beads may be used as bioaerosol receiving element.

In one embodiment regarding sampler for collecting bioaerosols, the impactor nozzle plate has a plurality of holes. In one aspect, the plurality of holes are evenly distributed from the center of the nozzle plate. In one aspect, the number of the holes may be in a range of 1 to infinite, 1-100, 1-50, 1-25, or 1-10.

In one embodiment regarding sampler for collecting bioaerosols, the bioaerosol receiving element holder further comprises an outlet configured to be connected to a vacuum pump.

In one embodiment regarding sampler for collecting bioaerosols, the sampler further comprises size-selective inlet that can remove larger particles. (e.g., a respirable cyclone (cut-off diameter of 4 µm) can be used to collect respirable dust. Industrial regulation is established based on respirable dust. Environmental regulation is based on PM 10 (<10 µm) and PM 2.5 (<2.5 µm). In this case, impactors can be used to remove particles larger than 10 µm and 2.5 µm). In one aspect, the size-selective inlet is a respirable cyclone. In one aspect, the respirable cyclone is configured to remove particles larger than 4 µm.

In one embodiment, bioaerosol receiving element is a swab. In one aspect, the swab is placed on a swab holder. The swab and the swab holder are positioned in the chamber.

In one embodiment, the impactor element comprises am impactor nozzle plate and an impactor housing. The impactor housing is adjacent to the chamber. In one aspect, the chamber has an outlet/inlet that allow the bioaerosol to pass through the impactor nozzle plate through the outlet/inlet and enter the chamber and to be adsorbed onto the swab.

In one embodiment, an optional size-selective inlet such as a respirable cyclone may be provided to remove particles bigger than about 1.0, 1.5, 2.0, 2.5, 3.0, 3.5, 4.0, 4.5, or 5.0 µm. In one aspect, the respirable cyclone may be provided to remove particles with a diameter of about 1.0-5.0 µm.

In one embodiment, the impactor can be modified to have a cut-off diameter ($d_{50}$) of about 200-800 nm, 300-1000 nm, 350-900 nm, 400-800 nm, 450-700 nm, 500-600 nm. In one aspect, the cut-off diameter is about 500-600 nm.

In one embodiment, the impactor nozzle plate has a plurality of holes with nozzle diameter (Dj) of about 200-800 µm, 300-1000 µm, 350-900 µm, 400-800 µm, 450-700 µm, or 500-600 µm. In one preferred aspect, the nozzle diameter is about 500-600 µm. In one embodiment, the respirable cyclone of the present disclosure has a cut-off diameter of about 4 µm or 5 µm.

In one embodiment, the present disclosure provides a non-cultivation bioaerosol detection method by collecting a bioaerosol sample with the novel sampler and directly measure the environmental microbe concentration, such as bacteria concentration, with adenosine triphosphate (ATP) bioluminescence assay.

Sampler Design and Fabrication

Figure 5:
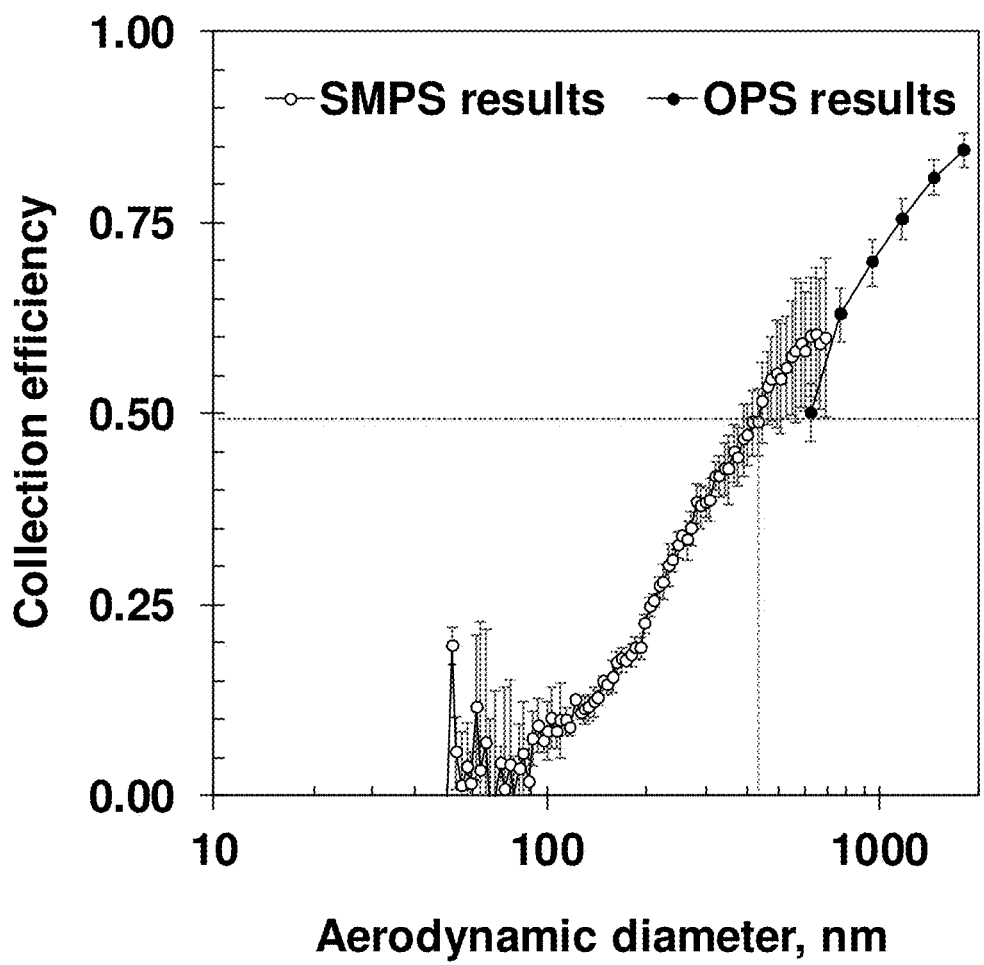
FIG. 5 shows the collection efficiency by particle size.

The most common collection methods for bioaerosols are inertial impaction methods. A particle-laden air is accelerated and directed by a nozzle of impactor toward an impaction plate, and the air is deflected around the edges of the plate toward an outlet. Since particles larger than the cut-off diameter have sufficient inertia to hurdle across the streamlines, they are collected onto the plate while particles smaller than the cut-off diameter follow the streamline. The present t disclosure designed and built a sampler to collect bioaerosols directly onto a swab head used for bioluminescence monitoring. The 50% cut-off diameter ($d_{50}$) of an impactor is the size at particles are collected with 50% efficiency. Collection efficiency increases for particles larger than the $d_{50}$ and decreases for smaller particles (S-shape collection efficacy curve by size as shown in FIG. 5 below). The target $d_{50}$ was set to 0.5 µm to collect even single small cell (1 µm).

Design and Fabrication of ATP Bioaerosol Sampler

Figure 3:
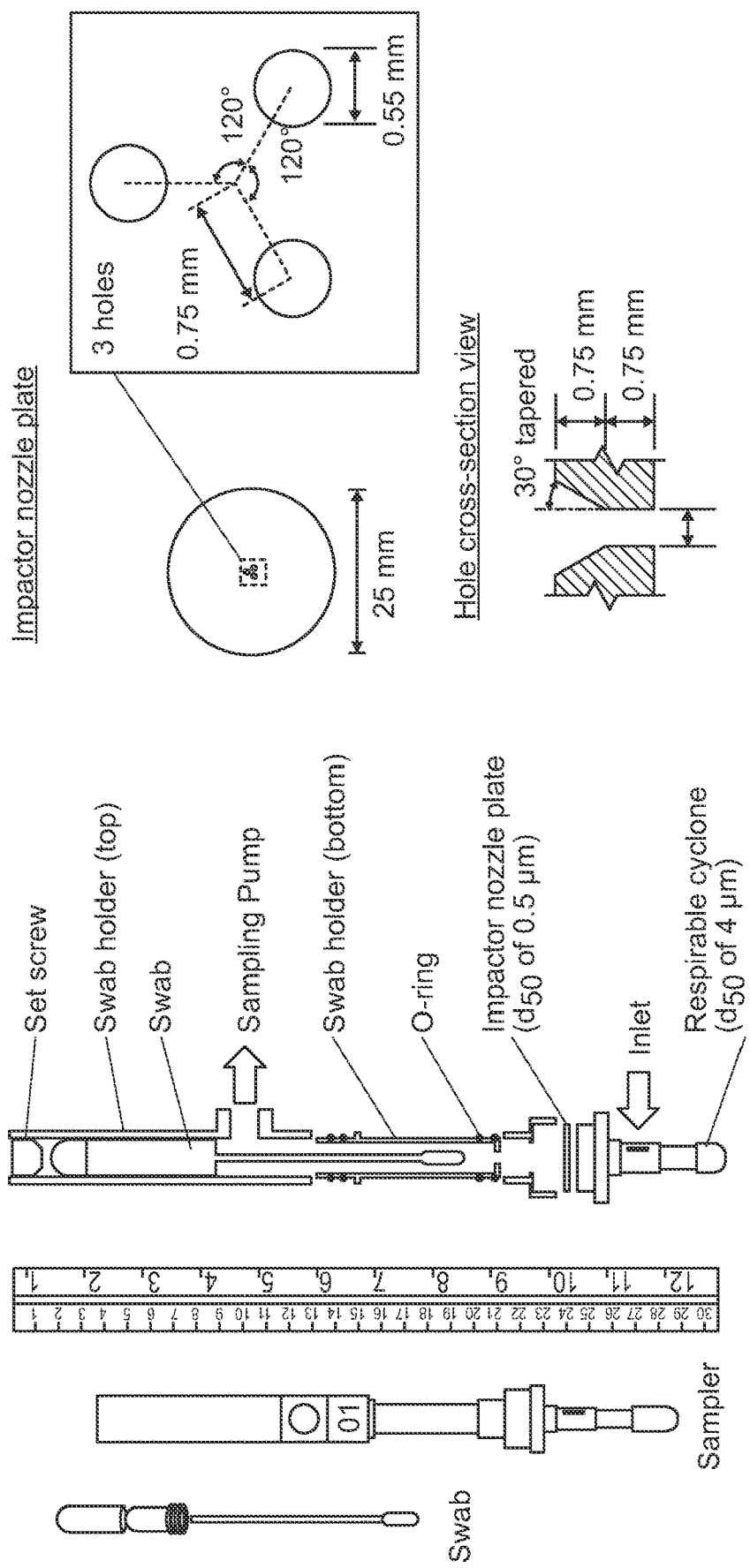
FIG. 3 shows the schematic of the ATP bioaerosol sampler of the present disclosure.

The schematic of the novel sampler structure can be found in FIG. 2 and FIG. 3. The sampler comprises a respirable cyclone, an impactor, and a swab holder. The respirable cyclone (225-01-01, SKC, USA) was used as a size-selective inlet to remove airborne particles bigger than 10 µm ($d_{50}$=4 µm). This part can be replaced to a PM2.5 or PM10 impactor for environmental health study. The impactor was designed to collect particles onto head of swab inserted in the holder. Particle-laden air were drawn into the respirable cyclone and the impactor using a vacuum pump at the flow rate of 2.5 L/min. All parts were made of autoclavable materials such as aluminum alloy or polyether ether ketone (PEEK).

Collection Efficacy Test

Figure 4:
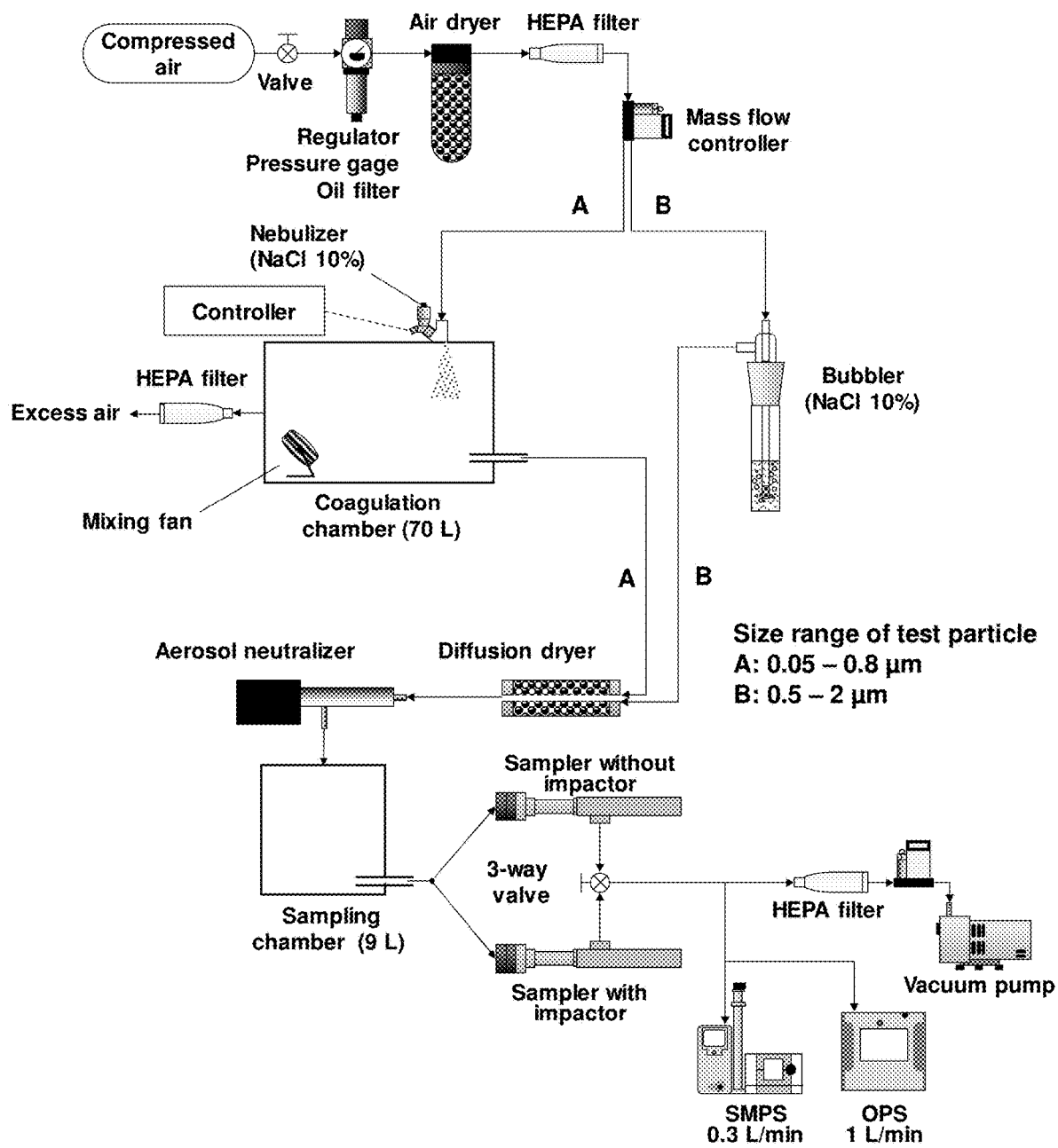
FIG. 4 shows the experimental setup for collection efficiency.

The experimental setup used to measure the collection efficiency and pressure drop of the impactor is shown in FIG. 4. To determine particle collection efficiency as a function of particle size, two aerosol generation systems were used to produce particles with different size distributions. A stream of particle-free compressed air from a dry particle-free air supply system consisting of an oil filter, an air dryer, and a high efficiency particulate air (HEPA) filter was controlled by a mass flow controller (MFC; model number, Alicat, USA) and delivered to a vibrating mesh nebulizer (Aeroneb Solo, Aerosgen, Ireland) or a bubbler (225-36-2, SKC, USA). Sodium chloride (NaCl) 10% solution (weight/volume) was filled in both nebulizer and bubbler. The NaCl aerosols from the nebulizer or the bubbler were passed through a diffusion dryer for water removal, were charge neutralized (3088, TSI Inc., USA). Subsequently, the NaCl aerosols were conveyed to the sampling chamber and were pulled through a three-way valve to passing through samplers. The sampler linked in the top line did not have the impactor nozzle plate or the swab while the other sampler in the bottom line had both of them. The respirable cyclone was not installed in the sampler during the collection efficiency test. Particle number concentrations at downstream of samplers were measured using a scanning mobility particle sizer (SMPS; 3938NL76, TSI Inc., USA) or an optical particle sizer (OPS; 3330, TSI, USA). Test particles produced from the nebulizer and the bubbler were measured using the SMPS (0.05-0.8 μm) and OPS (0.5-2 μm), respectively. The SMPS consisted of a classifier controller (3082, TSI Inc., USA), a differential mobility analyzer (DMA; 3081A, TSI Inc., USA), a condensation particle counter (CPC; 3776, TSI Inc., USA), and an aerosol neutralizer (3088; TSI Inc., USA). The mobility diameter ($d_m$) measured using the SMPS was converted to volume equivalent diameter ($d_{ve}$) as following equations:

$$d_{ve} = d_m \times \frac{C_c(d_{ve})}{\chi \times C_c(d_m)} \quad (1)$$

wherein $C_C$ is the Cunningham slip correction factor. $\chi$ is the dynamic shape factor and assumed to be 1.08 for salt particles. The $d_{ve}$ was then converted to aerodynamic diameter ($d_{ae}$) as follows:

$$d_{ae} = d_{ve} \times \sqrt{\frac{\rho_p \times C_c(d_{ve})}{\chi \times \rho_0 \times C_c(d_{ae})}} \quad (2)$$

wherein $\rho_0$ is the unit density (=1000 kg/m³) and $\rho_p$ is the particle density. The $\rho_p$ was assumed to be 2160 kg/m³ for salt particles. Optical diameter measured using the OPS has been assumed to be equal to $d_{ve}$ (Peters et al., 2006) and converted to $d_{ae}$ using the equation (2). The collection efficiency by size was calculated by the following equation:

$$\eta_c(d_{ae}) = 1 - \frac{C_s(d_{ae})}{C_b(d_{ae})} \quad (3)$$

wherein $C_s$ and $C_b$ are the number concentration of particles passing through the samplers with and without impactor nozzle plate and the swab. The measurement occurred in the following sequence: $C_{b1}$-$C_{s1}$-$C_{b2}$-$C_{s2}$-$C_{b3}$-$C_{s3}$-$C_{b4}$. For the equation (3), values of $(C_{b1}+C_{b2})/2$, $(C_{b2}+C_{b3})/2$ and $(C_{b3}+C_{b4})/2$ were used and then average of three $\eta_c$s was calculated. All the tests for the collection efficiencies were performed in same method.

Pressure drop of the sampler was measured using a Magnehelic Differential Pressure Gauge (2000-1000PA, Dwyer Instruments, USA).

Collection efficiency results are shown in FIG. 5. Experimental $d_{50}$ was about 0.440 μm and slightly smaller than theoretical $d_{50}$. Total pressure drop of sampler was 2.88±0.10 kPa.

Evaluation of ATP Bioaerosol Sampler by Comparison with Conventional Sampler

Figure 6:
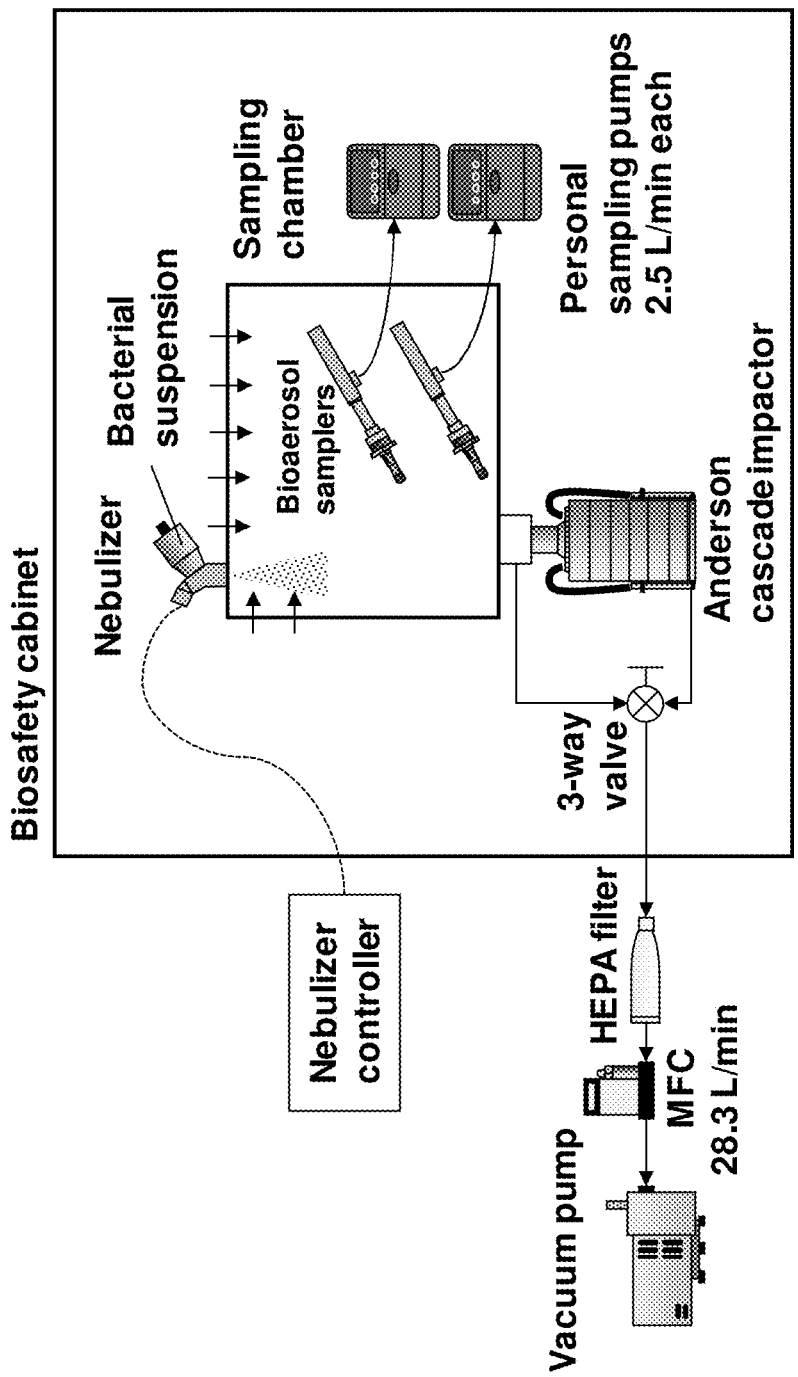
FIG. 6 shows the experimental setup for bioaerosol sampling in the lab.

Performance of ATP bioaerosol sampler was evaluated and compared with conventional sampler. The experimental setup is shown in FIG. 6. A vibrating mesh nebulizer (Aeroneb Solo System, Aerogen, Ireland) was used to aerosolize the E. coli suspension. The nebulizer was turned on and off (e.g., 0.25 sec on and 0.25 sec off) to control the concentration of E. coli droplets. For the collection of the aerosolized E. coli, two identical bioaerosol samplers were place in the sampling chamber (9 L) and connected to the personal sampling pumps (model, company, country) pulling the air at the flowrate of 2.5 L/min. Two different swabs, SuperSwab (Hygiena, LLC, USA) and UltraSwab (Hygiena, LLC, USA) were set in the samplers. After sampling the E. coli onto the swab head for two hours, the swab was placed into the swab tube. The swab tube was shaken several times for 3 sec after washing the swab head and mixing the collected bacteria with an ATP releasing reagent and a luminescence reagent for the light-generating reaction. The swab tube was placed in a bioluminometer (EnSURE, Hygiena, LLC, USA) to measure the RLUs from the sampled E. coli. RLUs were converted to CFUs using the conversion equation obtained from the swab calibration test. Since respirable cyclone was used in the ATP bioaerosol sampler, results from the sampler were expressed in respirable CFU concentrations. For calculating the concentration, CFUs were divided by sampling volume (sampling flow rate×sampling time).

For the comparison, a six-stage Anderson cascade impactor (TE-10-800, Tisch Environmental, USA) was employed as a conventional sampler. This instrument divides the bioaerosols into six fractions, in accordance with their aerodynamic diameters, as follows: ≥7.0 μm (1st stage), 7.0-4.7 μm (2nd), 4.7-3.3 μm (3rd), 3.3-2.1 μm (4th), 2.1-1.1 μm (5th) and 1.1-0.65 μm (6th). A Petri dish (diameter of 100 mm) containing agar (Difco nutrient agar, BD, USA) was utilized as the impacting substrate for each stage of the impactor. The sampling flow rate, sampling time, incubation temperature, and incubation time were 28.3/L/min, 1 min, 37° C., and 24 hours, respectively. After incubation, the CFU of each stage was counted. For the comparison, respirable concentration was calculated as follows:

$$CFU_{resp} = \Sigma_{i=1}^{6}(CFU_i \times F_r(d_i))$$

where i is the stage number and $F_r$ is the respirable fraction at midpoint size of stage i ($d_i$). Respirable CFU concentrations from ATP bioaerosol samplers and Anderson impactor were then compared.

Figure 7:
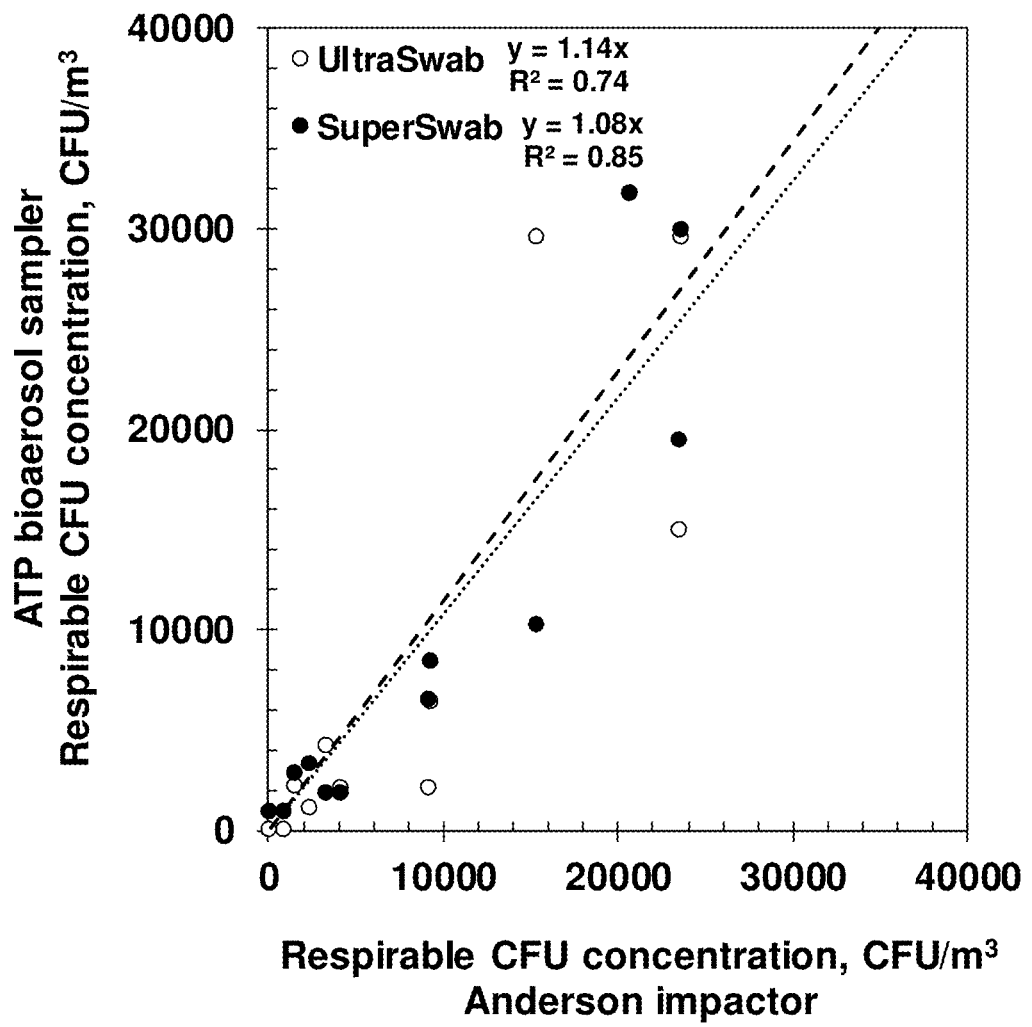
FIG. 7 shows the performance comparison results.
Figure 8:
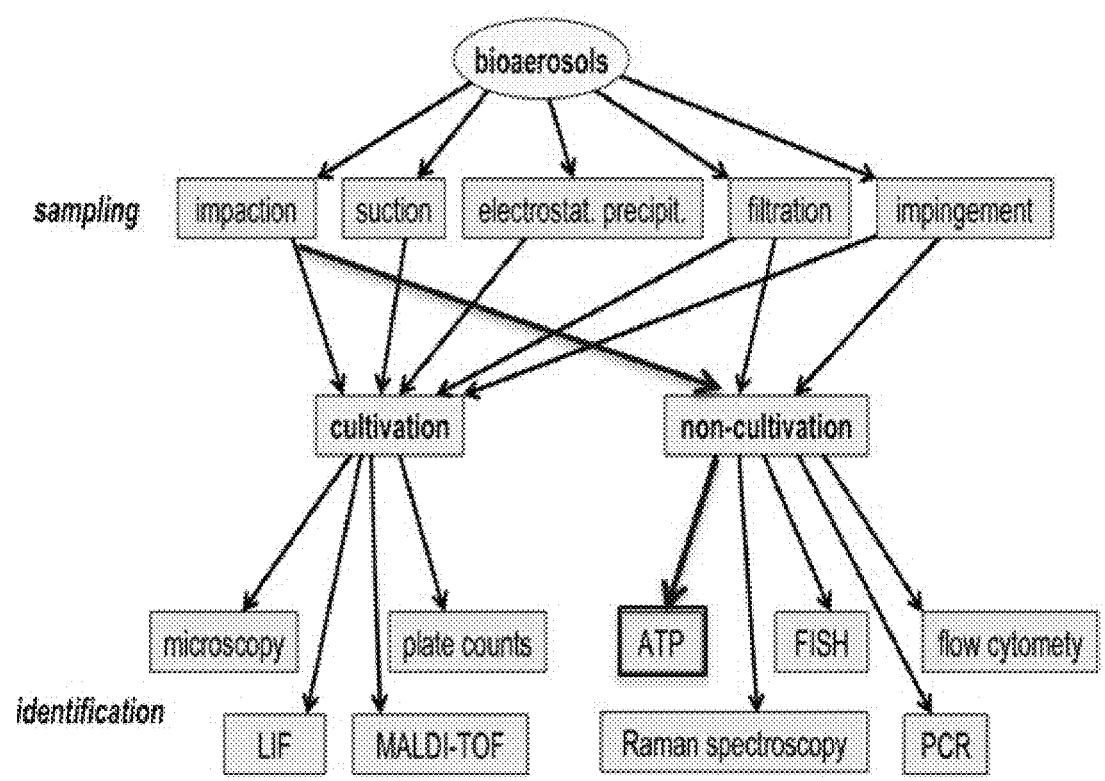
FIG. 8 shows sampling bioaerosol directly onto the ATP swab using an impactor, without the need of cultivation.

The results is shown in FIG. 7. Developed sampler shows similar results from conventional sampler. ATP samplers with both swabs were linearly correlated with the results from the Andersen impactor. SuperSwab ($R^2$=0.85) shows better correlation than UltraSwab ($R^2$=0.85) as shown in FIG. 7.

Therefore, the present disclosure provides a portable bioaerosols sampler that is capable of using an impactor to collect bioaerosols directly onto swab used in ATP bioluminometer. The sampler is much easier to implement logistically when compared with traditional sampler. One of the most important advantages of the present disclosure is sampling bioaerosol directly onto the ATP swab using an impactor, without the need of cultivation.

Those skilled in the art will recognize that numerous modifications can be made to the specific implementations described above. The implementations should not be limited to the particular limitations described. Other implementations may be possible.

We claim:
1. A sampler for collecting bioaerosols, wherein the sampler comprises: a) a bioaerosol receiving element that is a swab with a tip, which captures a bioaerosol sample onto the tip of the swab; b) a single stage impactor element with suitable size to allow the bioaerosol sample to pass, wherein the impactor element comprises an impactor nozzle plate and an impactor housing, wherein the impactor element has $d_{50}$ of 0.5-0.6 µm; and c) a bioaerosol receiving element holder comprising a top portion and a bottom portion, wherein the bottom portion comprises a plurality of seals such that the top portion sealably couples to the bottom portion and the bottom portion sealably couples to the impactor housing and sits flush within the impactor housing, and wherein the bottom portion comprises an opening in a center of a wall of the bottom portion and the opening is sized to receive the tip of the swab, wherein a portion of the tip is inserted into the; wherein the impactor element separates the bioaerosol receiving element and an outside environment from where the bioaerosol sample is collected.

2. The sampler of claim 1, wherein the impactor nozzle plate has a plurality of holes.

3. The sampler of claim 2, wherein the plurality of holes are evenly distributed from the center of the impactor nozzle plate.

4. The sampler of claim 2, wherein the plurality of holes have a nozzle diameter of 0.2-0.8 mm.

5. The sampler of claim 1, wherein the bioaerosol receiving element holder further comprises an outlet configured to be connected to a vacuum pump.

6. The sampler of claim 1, wherein the sampler further comprises a size selective inlet that is operable coupled to the impactor element and wherein the size-selective inlet is a respirable cyclone, a PM2.5 impactor, or a PM10 impactor.

7. A non-cultivation bioaerosol detection method comprising: collecting a bioaerosol sample with the sampler of claim 1; and measuring the bioaerosol sample concentration with an adenosine triphosphate (ATP) bioluminescence assay.

* * * * *